United States Patent
Hage et al.

(10) Patent No.: US 8,946,470 B2
(45) Date of Patent: Feb. 3, 2015

(54) METHOD FOR THE OXIDATION OF UNSATURATED ORGANIC COMPOUNDS

(75) Inventors: Ronald Hage, Leiden (NL); Johannes Wietse De Boer, Leiden (NL); Pattama Saisaha, Groningen (NL)

(73) Assignee: Catexel Limited, London (GB)

( * ) Notice: Subject to any disclaimer, the term of this patent is extended or adjusted under 35 U.S.C. 154(b) by 184 days.

(21) Appl. No.: 13/811,230

(22) PCT Filed: Jul. 21, 2011

(86) PCT No.: PCT/GB2011/001093
§ 371 (c)(1),
(2), (4) Date: Apr. 5, 2013

(87) PCT Pub. No.: WO2012/010842
PCT Pub. Date: Jan. 26, 2012

(65) Prior Publication Data
US 2013/0190528 A1    Jul. 25, 2013

(30) Foreign Application Priority Data
Jul. 21, 2010 (EP) .................................... 10170239

(51) Int. Cl.
C07C 51/16 (2006.01)
C07C 51/285 (2006.01)

(52) U.S. Cl.
CPC .................................... C07C 51/285 (2013.01)
USPC ....................................................... 562/407

(58) Field of Classification Search
None
See application file for complete search history.

(56) References Cited

U.S. PATENT DOCUMENTS 5,329,024 A    7/1994    Jureller et al.

FOREIGN PATENT DOCUMENTS

| CN | 101130170 A | 2/2008 |
| DE | 19923121 A1 | 11/2000 |
| WO | WO 03/059510 A2 | 7/2003 |
| WO | WO 2005/102971 A1 | 11/2005 |

OTHER PUBLICATIONS

Berkessel A. and Sklorz C A., "Mn-trimethyltriazacyclononane/ascorbic acid: a remarkably efficient catalyst for the epoxidation of olefins and the oxidation of alcohols with hydrogen peroxide", Tetrahedron Letters, 40, 7965-7968 (1999).
Che C-M et al., "Ruthenium-Catalyzed Oxidation of Alkenes, Alkynes, and Alcohols to Organic Acids with Aqueous Hydrogen Peroxide", Chem. Asian J., 1, 453-458 (2006).
De Boer J W. et al., "cis-Dihydroxylation and Epoxidation of Alkenes by [Mn2O(RCO2)2(tmtacn2]: Tailoring the Selectivity of a Highly H2O2-Efficient Catalyst", J. Am. Chem. Soc., 127, 7990-7991.
De Boer J W. , "The role of salicylic acid, L-ascorbic acid and oxalic acid in promoting the oxidation of alkenes with H2O2 catalysed by [MnIV2(O)3(tmtacn)2]2+†", Dalton Trans., 6283-6295 (2008).
De Vos D E. et al., "Epoxidation of Terminal or Electron-deficient Olefins with H2O2 catalysed by Mn-trimethyltriazacyclonane Complexes in the Presence of an Oxalate Buffer", Tetrahedron Letters, 39, 3221-3224 (1998).
Liu S-T et al., "Oxidative cleavage of alkenes catalyzed by a water/organic soluble manganese porphyrin complex", Tetrahedron, 63, 1821-1825 (2007).
Noyori R. et al., "A "Green" Route to Adipic Acid: Direct Oxidation of Cyclohexenes with 30 Percent Hydrogen Peroxide", Science, 281, 1646-1647 (1998).
Noyori R. et al., "Green oxidation with aqueous hydrogen peroxide", Chem. Commun., 1977-1986 (2003).
Olah G A. et al., "Synthetic Methods and Reactions; 68. Nafion-H-Catalyzed Hydration and Methanolysis of Epoxides", Synthesis, 280-282 (Apr. 1981).
Ranu B C. et al., "Indium (III) chloride-catalyzed oxidative cleavage of carbon-carbon multiple bonds by *tert*-butyl hydroperoxide in water-a safer alternative to ozonolysis", Tetrahedron Letters, 49, 2588-2591 (2008).
Shal'Pin G B. et al., "Oxidation with the 'O2-H2O2-vanadium complex-pyrazine-2-carboxylic acid' reagent", Russian Chemical Bulletin, 48(5) 896-899 (1999).
Tromel V M and Russ M., Angew. "Dimanganheptoxid zur selektiven Oxidation organischer Substarte", Chem., 99(10), 1037-1038 (1987).
Extended European Search Report re Application No. 10170239.7—2103 Dated Dec. 14, 2010 in 8 pages.
International Search Report and Written Report re International Application No. PCT/GB2011/001093 Mailed on Nov. 24, 1022 in 14 pages, 2011.

*Primary Examiner* — Sudhakar Katakam
*Assistant Examiner* — Jennifer C Sawyer
(74) *Attorney, Agent, or Firm* — Knobbe, Martens, Olson & Bear, LLP

(57) ABSTRACT

A one-pot method for the oxidative cleavage of unsaturated carbon-carbon bonds to provide a carboxylic acid or a ketone-containing compound is disclosed. The method comprises contacting an alkene or an alkyne with hydrogen peroxide and a manganese transition metal catalyst having a ligand of formula (I):

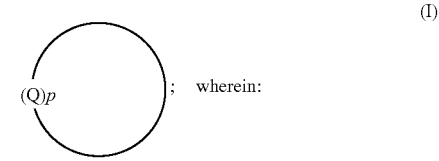

wherein:

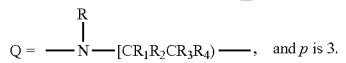

$Q = -\overset{R}{\underset{|}{N}}-[CR_1R_2CR_3R_4]-$, and $p$ is 3.

25 Claims, No Drawings

METHOD FOR THE OXIDATION OF UNSATURATED ORGANIC COMPOUNDS

FIELD

The present invention concerns a method for the oxidative cleavage of unsaturated carbon-carbon bonds into carbonyl compounds.

BACKGROUND

Carboxylic acids are industrially useful chemicals used both as end-products and as starting materials in a variety of different processes. Examples of dicarboxylic acids include glutaric acid, a common precursor for plasticers and polyesters. Also suberic acid (hexane-1,6-dicarboxylic acid) and adipic acids are useful precursors for different chemicals, such as polyamide resins or nylon 6-6.

Adipic acid (1,6-hexanedioic acid) is an organic compound with the formula $(CH_2)_4(COOH)_2$. From an industrial perspective, it is the most important dicarboxylic acid. About 2.5 billion kilograms of adipic acid is produced annually; the main use for adipic acid is as a precursor for the production of nylon.

R. Noyori and co-workers, *Science*, 281, 1646-1647 (1998), discloses that adipic acid may be produced from the oxidation of cyclohexanol or cyclohexanone with nitric acid.

R. Noyori et al., *Chem. Commun.*, 1977-1986 (2003), discloses an oxidative system which employs a tungstate, hydrogen peroxide and a quaternary ammonium phase-transfer catalyst to get efficient cleavage of an alkene.

C.-M. Che, et al., *Chem. Asian J.*, 1, 453-458 (2006), discloses that Ruthenium complexes containing 1,4,7-trimethyl-1,4,7-triazacyclononane with hydrogen peroxide furnishes dicarboxylic acid from different alkenes.

J. W. de Boer et al., *Dalton Transactions*, 6283-6295 (2008) discloses that suberic acid can be formed from cis-1, 2-cyclooctanedi-ol and hydrogen peroxide and a dinuclear Mn catalyst with 1,4,7-trimethyl-1,4,7-triazacyclononane; and that epoxidation and/or cis-dihydroxylation of alkenes can be performed using a dinuclear Mn catalyst with 1,4,7-trimethyl-1,4,7-triazacyclononane in the presence of either L-ascorbic acid or dehydroascorbic acid.

A. Berkessel and C. A. Sklorz, *Tetrahedron Letters*, 40, 7965-7968 (1999) describe the use of a combination of a Mn-salt, 1,4,7-trimethyl-1,4,7-triazacyclononane, ascorbic acid and/or sodium ascorbate as catalyst system for the epoxidation of alkenes and the oxidation of primary and secondary alcohols.

SUMMARY

We have found that treating unsaturated compounds constituted by aliphatic and aromatic compounds containing unsaturated bonds, in particular carbon-carbon double or triple bonds, with a manganese catalyst and hydrogen peroxide yields carboxylic acid or ketone-containing molecules. This is resultant from cleavage of the carbon-carbon double and/or triple bond(s). Whilst cyclic unsaturated molecules furnish molecules containing two carboxylic acid groups, acyclic molecules form molecules containing one carboxylic acid group.

If the carbon atoms (sp2) involved in the unsaturated bond have an additional group not being hydrogen, a ketone will be formed. In other words, if neither of the two substituents of a carbon atom of a C=C bond in an alkene is hydrogen, oxidative cleavage of the C=C bond according to this invention will afford a ketone-containing compound, the carbon atom of which derives from the carbon atom of the original C=C bond which is not substituted with hydrogen.

In chemistry, a one-pot synthesis/reaction is a strategy to improve the efficiency of a chemical reaction whereby a reactant is subjected to successive chemical reactions in just one reactor. This is much desired by chemists because avoiding a lengthy separation process and purification of the intermediate chemical compound would save time and resources while increasing chemical yield.

In one aspect the present invention provides a one-pot method for the oxidative cleavage of an alkene or alkyne whereby to provide a carboxylic acid or a ketone-containing compound, the method comprising contacting the alkene or alkyne with a catalytic oxidation system comprising (i) hydrogen peroxide, (ii) a manganese transition metal catalyst of a ligand of the of formula (I):

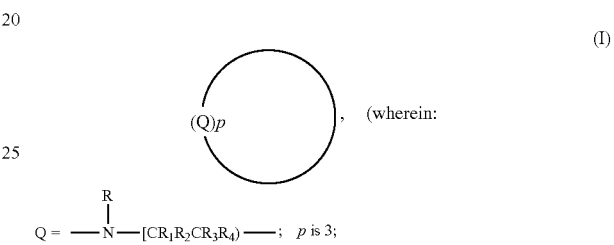

(wherein:

$Q = -\overset{R}{\underset{|}{N}}-[CR_1R_2CR_3R_4]-$ ; $p$ is 3;

R is independently selected from: hydrogen, C1-C6-alkyl, C2OH, C1COOH, and pyridin-2-ylmethyl or one of R is linked to the N of another Q from another ring via an ethylene or propylene bridge, for example an ethylene bridge; R1, R2, R3, and R4 are independently selected from: H, C1-C4-alkyl, and C1-C4-alkylhydroxy) and (iii) a carboxylic acid, carboxylate salt or mixture thereof; or ascorbic acid, or a salt or ester thereof, or mixture thereof, wherein the molar ratio of hydrogen peroxide to the alkene or the alkyne is from 20:1 to 1:1 and the catalyst is present in a range from 0.0001 to 5 mol % with respect to the alkene or the alkyne.

In another aspect the present invention provides a one-pot process for the production of adipic acid comprising the following steps:

contacting cyclohexene with a catalytic oxidation system comprising (i) hydrogen peroxide, (ii) a manganese transition metal catalyst of a ligand of formula (I):

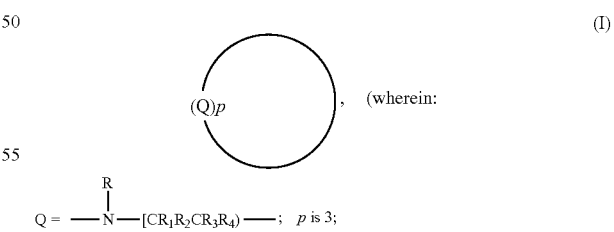

(wherein:

$Q = -\overset{R}{\underset{|}{N}}-[CR_1R_2CR_3R_4]-$ ; $p$ is 3;

R is independently selected from: hydrogen, C1-C6-alkyl, C2OH, C1COOH, and pyridin-2-ylmethyl or one of R is linked to the N of another Q from another ring via an ethylene or propylene bridge, for example an ethylene bridge; R1, R2, R3, and R4 are independently selected from: H, C1-C4-alkyl, and C1-C4-alkylhydroxy) and (iii) a carboxylic acid, carboxylate salt or mixture thereof; or ascorbic acid, or a salt or ester thereof, or mixture thereof, wherein the molar ratio of hydrogen peroxide to cyclohexene is from 20:1 to 1:1 and the catalyst is present in a range from 0.0001 to 5 mol % with respect to cyclohexene; and optionally working-up the product of the one-pot process.

DETAILED DESCRIPTION

Where the unsaturated compound is an alkene, the carbon-carbon double bond is not part of an aromatic ring but may be conjugated therewith. For example, the unsaturated compound may be styrene. The unsaturated compound is an alkene or alkyne. Preferably the unsaturated compound is an alkene. Most preferably the alkene is a cycloalkene having a single double bond.

With the catalyst of a ligand of formula (I) comprises one group R is linked to the N of another Q from another ring via an ethylene or propylene bridge, it will be understood that such ligands of formula (I) may alternatively be represented by the following structure:

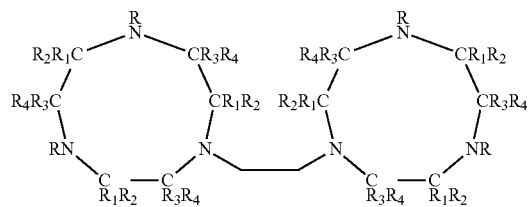

and a homologous structure having a propylene bridge between the two rings, wherein R, R1, R2, R3, and R4 are as herein defined.

In particular embodiments in which the catalyst of a ligand of formula (I) comprises one group R linked to the N of another Q from another ring via a bridge, the bridge is an ethylene bridge.

The preferred ligands of the transition metal catalyst are 1,4,7-trimethyl-1,4,7-triazacyclononane (Me$_3$-TACN) and 1,2-bis-(4,7-dimethyl-1,4,7-triazacyclonon-1-yl)-ethane (Me$_4$-DTNE).

Preferably the manganese complex is dinuclear and is of the oxidation state selected from II-II, II-III, III-III, III-IV, and IV-IV. Preferably the manganese complex contains one or more oxygen or carboxylate bridges.

The preformed transition metal catalyst is preferably a dinuclear Mn(III) or Mn(IV) complex, e.g. a dinuclear Mn(III)Mn(IV) complex, with at least one O$^{2-}$ bridge. For example, the transition metal catalyst may be a salt of the metal complexes [(Mn$^{IV}$)$_2$($\mu$-O)$_3$(Me$_3$-TACN)$_2$]$^{2+}$, [(Mn$^{III}$)$_2$($\mu$-O)($\mu$-CH$_3$COO)$_2$(Me$_3$-TACN)$_2$]$^{2+}$ or [Mn$^{III}$Mn$^{IV}$($\mu$-O)$_2$($\mu$-CH$_3$COO)(Me$_4$-DTNE)]$^{2+}$.

The manganese transition metal catalyst used may be non-deliquescent by using counter ions such as PF$_6^-$ or ClO$_4^-$. Alternatively, the preformed transition metal may be in the form of a salt such that it has a water solubility of at least 50 g/l at 20° C., as described in WO 2006/125517. Examples of suitable salts are those of chloride, acetate, sulfate, benzoate and nitrate. Alternatively, C$_{1-3}$alkylbenzene sulfonate salts, for example tosylate and cumene sulfonate salts, as are described in WO 2011/066934 A2 and WO 2011/066935 A2, may be used.

The manganese catalyst may be added in total at the beginning of the reaction or can be dosed during the reaction continuously or added batch-wise over the time course of the reaction.

The unsaturated compound does not need to be completely miscible in any water present in the reaction system but it is preferred that it is miscible to some extent. Indeed the unsaturated compound may be liquid or solid and will be taken into the reaction as the unsaturated compound is depleted.

Water is generally present in the reaction by virtue of the addition of the hydrogen peroxide which is commercially available as 50 wt % and 30 wt % aqueous solutions. However this does not exclude the use of 100% hydrogen peroxide in the one-pot reaction. Also not excluded is the use of aqueous solutions of hydrogen peroxide having hydrogen peroxide concentrations of less than 30 wt %. The reaction mixture may be substantially aqueous with the unsaturated compound present as second phase that is drawn into the reaction by virtue of small miscibility. Preferably, the one-pot reaction, has at least 2% wt water present.

The method is typically practised wherein hydrogen peroxide to unsaturated compound ratio is from 20:1 to 4:1 or 10:1 to 2:1 (as calculated for neat hydrogen peroxide), preferably from 6:1 to 3:1; the optimal ratio is 4:1.

In some embodiments, the invention may be practised so as to work up (discussed below) the mixture resultant from the method without purification and subjecting the resultant mixture to a further method (reaction) of the invention. In this way, any unreacted alkene or alkyne from the previous reaction(s) can be subjected to an additional reaction whereby to increase the ultimate yield of the product(s) of oxidative cleavage. After the final oxidative cleavage reaction, the resultant mixture can be worked up with purification, whereby to provide the desired reaction product(s)

Preferably the catalyst dosage is from 0.001 and 1 mol % with respect to the unsaturated compound.

The reaction mixture preferably contains water. In this regard, depending upon the unsaturated compound being oxidised (i.e. subjected to oxidative cleavage according to this invention) and the nature of any solvent being used, the reaction may be a single phase or bi-phase. Alternatively, the reaction may be triphasic if, for example, the unsaturated compound to be oxidised is only partially soluble in a bi-phasic reaction medium.

The presence of a further solvent is preferred and in this regard acetonitrile, methanol, ethanol, t-butanol, methylethylketone and water are preferred solvents. When the unsaturated compound is a solid at the temperatures the one-pot method, is preferably conducted in the presence of another solvent other than water.

When the product (ketone or carboxylic acid) is produced it may also come out of the reaction mixture and the reaction will become a bi- or tri-phase reaction.

The pH of the aqueous phase of the one pot reaction is preferably from 0 to 12, more preferably from 1 to 7.

The one-pot reaction is preferably conducted in the temperature range from 0 to 80° C., more preferably from 4 to 60° C.

In some embodiments of the invention, a carboxylic acid, a carboxylate salt, or a mixture of a carboxylic acid and carboxylate salt are present in the one-pot method, i.e. a carboxylic acid, a carboxylate salt, or a mixture of a carboxylic acid and carboxylate salt constitute component (iii) of the catalytic oxidation system defined herein.

In other embodiments, component (iii) of the catalytic oxidation system is ascorbic acid, or a salt or ester thereof, or a mixture thereof. In still further embodiments, component (iii) of the catalytic oxidation system may comprise both a carboxylic acid, or a carboxylate salt, or a mixture of a carboxylic acid and carboxylate salt; and ascorbic acid, or a salt or ester thereof, or a mixture thereof.

Where present, carboxylic acids or carboxylate salts are preferably oxalic acid, benzoic acids (e.g. benzoic acid itself) and trichloroacetic acid, or salts thereof. The benzoic acid may have further substituents and in this regard 2,6-dichlorobenzoic acid is preferred. Alternatively, the carboxylic acid may be used which is the same as the one formed after C=C cleavage. For example, when using 1-octene as substrate, 1-heptane-carboxylic acid can be used as co-catalyst. The preferred salts (carboxylates) are those of the alkali metals and in particular sodium and potassium.

Where present, the molar ratio of carboxylic acid/carboxylate to the manganese transition metal catalyst is preferably in the range from 2 to 100:1, for example from 5 to 100:1, more preferably from 5 to 60:1 or from 10 to 60:1 and most preferably from 10 to 30:1, for example 30:1. It will be understood that these molar ratios are initial ratios since, as the reaction progresses, the concentration of carboxylic acid(s) will increase and, dependent upon the catalyst loading, the molar ratio of the product carboxylic acid:catalyst will typically rapidly exceed 100:1.

Where present, ascorbate salts may be any convenient metal (e.g. alkali metal) salt, such as sodium ascorbate, potassium ascorbate, magnesium (di)ascorbate and calcium (di)ascorbate. Esters of ascorbic acid and ascorbate salts may be, for example, eters of saturated or unsaturated fatty acids, such as esters of $C_{6-50}$ fatty acids, for example, ascorbyl palmitate or ascorbate stearate. Where present, the molar ratio of ascorbic acid, or a salt or ester thereof, or a mixture thereof, to the manganese transition metal catalyst is preferably in the range from 1 to 100:1, more preferably from 5 to 60:1 and most preferably from 10 to 30:1.

Where component (iii) of the catalytic oxidation system comprises both a carboxylate salt, or a mixture of a carboxylic acid and carboxylate salt; and ascorbic acid, or a salt or ester thereof, or a mixture thereof, the combined molar ratio of the constituents of component (iii) of the catalytic oxidation system to the manganese transition metal catalyst is preferably in the range from 1 to 100:1, more preferably from 5 to 60:1 and most preferably from 10 to 30:1.

The unsaturated compound is preferably an alkene. Preferably the alkene has at least one vinylic hydrogen. Preferably the alkene has at least two vinylic hydrogens. Preferably the alkene has a double bond that has two vinylic hydrogens, for example in which each carbon atom of the C=C bond has one hydrogen atom. Preferably the alkene only has one double bond.

Most preferably the alkene is mono-cyclic and has a single double bond. Examples of this type of molecule are cyclooctene and cyclohexene.

Cyclooctene is exemplified below where the two vinylic hydrogens of the double bond are exemplified.

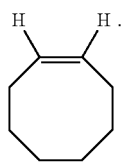

The exemplified Cyclooctene has at least two vinylic hydrogens and only one point of unsaturation.

The mixture resultant from carrying out a one-pot method of the invention may be worked up with or without purification and submitted to an additional one-pot method of the invention. Where purification is carried out, this allows any unreacted alkene or alkyne to be separated from the product(s) of oxidative cleavage and subjected to a further one-pot method of the invention.

Most preferably the reaction is worked up after the one pot method to form either the carboxylic acid or ketone.

The term worked-up is known in the art. In chemistry work-up refers to the series of manipulations required to isolate and purify the product(s) of a chemical reaction. Typically, these manipulations include:
 quenching a reaction to deactivate any unreacted reagents
 changing the pH to prevent further reaction
 cooling the reaction mixture or adding an antisolvent to induce precipitation, and collecting or removing the solids by filtration, decantation, or centrifuging
 removal of solvents by evaporation
 separating the reaction mixture into organic and aqueous layers by liquid-liquid extraction
 purification by chromatography, distillation or recrystalisation.

The invention may be further understood with reference to the following non-limiting clauses:

1. A one-pot method for the preparation of a carboxylic acid from an unsaturated compound, the method comprising the step of contacting the unsaturated compound with hydrogen peroxide and a manganese transition metal catalyst of a ligand of the of formula (I):

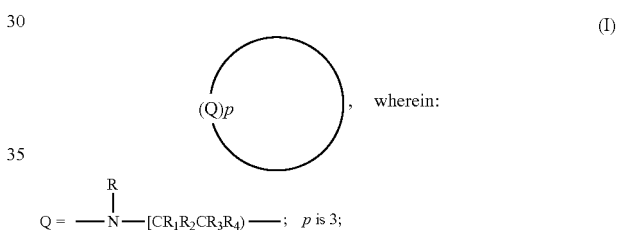

R is independently selected from: hydrogen, C1-C6-alkyl, C2OH, C1COOH, and pyridin-2-ylmethyl or one of R is linked to the N of another Q from another ring via an ethylene bridge; R1, R2, R3, and R4 are independently selected from: H, C1-C4-alkyl, and C1-C4-alkylhydroxy, wherein the ratio of hydrogen peroxide to alkene is from 20:1 to 1:1 and the catalyst is present in a range from 0.0001 to 5 mol % with respect to the alkene.

2. A one-pot method according to clause 1, wherein the hydrogen peroxide to alkene ratio is from 10:1 to 2:1.

3. A one-pot method according to clause 2, wherein the hydrogen peroxide to alkene ratio is from 6:1 to 3:1.

4. A one-pot method according to any one of the preceding clauses, wherein the catalyst dosage is from 0.001 and 1 mol % with respect to the unsaturated compound.

5. A one-pot method according to any one of the preceding clauses, wherein the ligand is selected from 1,4,7-trimethyl-1,4,7-triazacyclononane (Me$_3$-TACN), 1,2-bis-(4,7-dimethyl-1,4,7-triazacyclonon-1-yl)-ethane (Me$_4$-DTNE).

6. A one-pot method according to any one of the preceding clauses, wherein the manganese complex is dinuclear and is of the oxidation state selected from II-II, II-III, III-III, III-IV, and IV-IV and contains one or more oxygen or carboxylate bridges.

7. A one-pot method according to any one of the preceding clauses, wherein a carboxylic acid, a carboxylate salt, or a mixture of a carboxylic acid and carboxylate salt is present in the catalytic oxidation system.

8. A one-pot method according to clause 7, wherein the carboxylic acid or salt thereof is selected from: oxalic acid, benzoic acid; 2,6-dichlorobenzoic acid and, trichloroacetic acid.
9. A one-pot method according to any one of the preceding clauses, wherein ascorbic acid is present in the catalytic oxidation system.
10. A one-pot method according to any one of the preceding clauses, wherein the reaction is carried out in the presence of solvent selected from: acetonitrile, methanol, ethanol, t-butanol, and water.
11. A one-pot method according to any one of the preceding clauses, wherein the unsaturated compound is an alkene.
12. A one-pot method according to clause 11, wherein the alkene has at least one vinylic hydrogen.
13. A one-pot method according to clause 12, wherein the alkene has at least two vinylic hydrogens.
14. A one-pot method according to clause 13, wherein the alkene has at least two vinylic hydrogens and only point of unsaturation.
15. A one-pot method according to clause 14, wherein the alkene is mono-cyclic and has a single double bond.
16. A one-pot method according to clause 15, wherein the alkene is selected from: cyclooctene and cyclohexene.
17. A one-pot method according to clause 12, wherein a carboxylic acid or alkali metal salt thereof is present, the carboxylic acid being that same as an oxidation product of the one-pot reaction.
18. A one-pot process for the production of adipic acid comprising the following steps:
(i) contacting cyclohexene with hydrogen peroxide and a manganese transition metal catalyst of a ligand of the of formula (I):

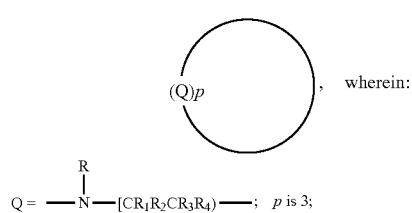

wherein:

$Q = $ —N—[$CR_1R_2CR_3R_4$]—— ; p is 3;

R is independently selected from: hydrogen, C1-C6-alkyl, C2OH, C1COOH, and pyridin-2-ylmethyl or one of R is linked to the N of another Q from another ring via an ethylene bridge; R1, R2, R3, and R4 are independently selected from: H, C1-C4-alkyl, and C1-C4-alkylhydroxy, wherein the ratio of hydrogen peroxide to alkene is from 20:1 to 1:1 and the catalyst is present in a range from 0.0001 to 5 mol % with respect to cyclohexene; and,
optionally (ii) working-up the product of the one-pot process.
19. A one-pot process for the production of adipic acid according to clause 18, with the limitations of any one of clauses 2 to 10.

The following examples will more fully illustrate the embodiments of this invention.

EXPERIMENTAL

Experiment 1

Cyclooctene→Suberic Acid

To a mixture of [$Mn_2O_3(Me_3\text{-}TACN)_2$] ($PF_6$)$_2$.$H_2O$ (16.2 mg, 20 μmol) and 2,6-dichlorobenzoic acid (114.6 mg, 0.60 mmol) in $CH_3CN$ (14 ml) was added $H_2O_2$ (60 μl of a 50% aq. solution, 1.06 mmol) at room temperature and the resulting mixture was stirred for 20 min. Subsequently cyclooctene (20 mmol) was added together with $CH_3CN$ (4 ml) and water (2 ml). $H_2O_2$ (4.53 ml of a 50% aq. solution, 80 mmol) was then added at room temperature using a syringe pump (0.14 ml/hr). A second amount of [$Mn_2O_3(Me_3\text{-}TACN)_2$] ($PF_6$)$_2$.$H_2O$ (16.2 mg, 20 μmol) was added to the reaction mixture 24 hours after the addition of hydrogen peroxide had commenced. When the addition of hydrogen peroxide was completed, the mixture was stirred for an additional hour. Water (10 ml) and diethyl ether (10 ml) were added and the pH of the aqueous layer was set to pH >10 by adding some 4 M NaOH (aq.). The organic layer was separated and the aqueous layer was washed with diethyl ether (3×15 ml). The pH of the aqueous layer was subsequently set to pH <1.5 with some 10% HCl (aq.) and was extracted with diethyl ether (5×10 ml). The combined extracts were washed with brine (15 ml) and subsequently dried over anhydrous $Na_2SO_4$. The solvents were evaporated in vacuo yielding 0.95 g of a solid with a purity of circa 84% (determined by $^1H$ NMR). Suberic acid was thus obtained in about 23% yield. $^1H$ NMR (400 MHz, acetone-d6): δ 1.39-1.43 (m, 4H), 1.61-1.66 (m, 4H), 2.34 (t, J=7.5 Hz, 4H), 10.5 (br s, 2H). N.B. NMR showed other compounds as well, including 2,6-dichlorobenzoic acid Experiment 2

Cyclohexene→Adipic Acid

To a mixture of [$Mn_2O_3(Me_3\text{-}TACN)_2$] ($PF_6$)$_2$.$H_2O$ (8.1 mg, 10 μmol) and 2,6-dichlorobenzoic acid (57.3 mg, 0.30 mmol) in $CH_3CN$ (7 ml) was added $H_2O_2$ (30 μl of a 50% aq. solution, 0.53 mmol) at room temperature and the resulting mixture was stirred for 20 min. Subsequently cyclohexene (821 mg, 10 mmol) was added together with $CH_3CN$ (3 ml). $H_2O_2$ (3.22 ml of a 50% aq. solution, 56.8 mmol) was then added at room temperature using a syringe pump (0.14 ml/hr). A second amount of [$Mn_2O_3(Me_3\text{-}TACN)_2$] ($PF_6$)$_2$.$H_2O$ (8.1 mg, 10 μmol) was added to the reaction mixture 8 hours after the addition of hydrogen peroxide had commenced. When the addition of hydrogen peroxide was completed, the mixture was stirred for an additional hour. Water (10 ml) and diethyl ether (10 ml) were added and the pH of the aqueous layer was set to pH >10 by adding some 4 M NaOH (aq.). The organic layer was separated and the aqueous layer was washed with diethyl ether (3×15 ml). The pH of the aqueous layer was subsequently set to pH <1.5 with some 10% HCl (aq.) and was extracted with diethyl ether (5×10 ml). The combined extracts were washed with brine (15 ml) and subsequently dried over anhydrous $Na_2SO_4$. The solvents were evaporated in vacuo yielding 0.215 g of a solid with a purity of circa 59% (determined by $^1H$ NMR). Adipic acid was thus obtained in about 9% yield. $^1H$ NMR (400 MHz, DMSO-d6): δ 1.48-1.52 (m, 4H), 2.19-2.26 (m, 4H). N.B. NMR showed other compounds as well, including 2,6-dichlorobenzoic acid.

Experiment 3

1-Octene→Hexanoic Acid

To a mixture of [$Mn_2O_3(Me_3\text{-}TACN)_2$] ($PF_6$)$_2$.$H_2O$ (8.1 mg, 10 μmol) and 2,6-dichlorobenzoic acid (57.3 mg, 0.30 mmol) in $CH_3CN$ (7 ml) was added $H_2O_2$ (30 μl of a 50% aq. solution, 0.53 mmol) at room temperature and the resulting mixture was stirred for 20 min. Subsequently, 1-octene (1.12 g, 10 mmol) was added together with CH$_3$CN (3 ml). H$_2$O$_2$ (3.22 ml of a 50% aq. solution, 56.8 mmol) was then added at room temperature using a syringe pump (0.14 ml/hr). A second amount of [Mn$_2$O$_3$(Me$_3$-TACN)$_2$] (PF$_6$)$_2$.H$_2$O (8.1 mg, 10 μmol) was added to the reaction mixture 8 hours after the addition of hydrogen peroxide had commenced. When the addition of hydrogen peroxide was completed, the mixture was stirred for an additional hour. Water (10 ml) and diethyl ether (10 ml) were added and the pH of the aqueous layer was set to pH >10 by adding some 4 M NaOH (aq.). The organic layer was separated and the aqueous layer was washed with diethyl ether (3×15 ml). The pH of the aqueous layer was subsequently set to pH <1.5 with some 10% HCl (aq.) and was extracted with diethyl ether (5×10 ml). The combined extracts were washed with brine (15 ml) and subsequently dried over anhydrous Na$_2$SO$_4$. The solvents were evaporated in vacuo yielding 0.193 g of a solid with a purity of circa 65% (determined by $^1$H NMR). Heptanoic acid was thus obtained in about 10% yield. $^1$H NMR (400 MHz, acetone-d6): δ 0.91-0.96 (m, 3H), 1.33-1.40 (m, 6H), 1.61-1.65 (m, 2H), 2.29-2.33 (m, 2H). N.B. NMR showed other compounds as well, including 2,6-dichlorobenzoic acid.

Experiment 4

Styrene→Benzoic Acid

To a mixture of [Mn$_2$O$_3$(Me$_3$-TACN)$_2$] (PF$_6$)$_2$.H$_2$O (8.1 mg, 10 μmol) and 2,6-dichlorobenzoic acid (57.3 mg, 0.30 mmol) in CH$_3$CN (7 ml) was added H$_2$O$_2$ (30 μl of a 50% aq. solution, 0.53 mmol) at room temperature and the resulting mixture was stirred for 20 min. Subsequently, styrene (1.04 g, 10 mmol) was added together with CH$_3$CN (3 ml). H$_2$O$_2$ (3.22 ml of a 50% aq. solution, 56.8 mmol) was then added at room temperature using a syringe pump (0.14 ml/hr). A second amount of [Mn$_2$O$_3$(Me$_3$-TACN)$_2$] (PF$_6$)$_2$.H$_2$O (8.1 mg, 10 μmol) was added to the reaction mixture 8 hours after the addition of hydrogen peroxide had commenced. When the addition of hydrogen peroxide was completed, the mixture was stirred for an additional hour. Water (10 ml) and diethyl ether (10 ml) were added and the pH of the aqueous layer was set to pH >10 by adding some 4 M NaOH (aq.). The organic layer was separated and the aqueous layer was washed with diethyl ether (3×15 ml). The pH of the aqueous layer was subsequently set to pH <1.5 with some 10% HCl (aq.) and was extracted with diethyl ether (5×10 ml). The combined extracts were washed with brine (15 ml) and subsequently dried over anhydrous Na$_2$SO$_4$. The solvents were evaporated in vacuo yielding 0.100 g of a solid with a purity of circa 41% (determined by $^1$H NMR). Benzoic acid was thus obtained in about 3% yield. $^1$H NMR (400 MHz, acetone-d6): δ 7.53-7.58 (m, 2H), 7.65-7.70 (m, 1H), 8.08-8.10 (m, 2H). N.B. NMR showed other compounds as well, including 2,6-dichlorobenzoic acid.

Experiment 5

1-Octyne→Hexanoic Acid

To a mixture of [Mn$_2$O$_3$(Me$_3$-TACN)$_2$] (PF$_6$)$_2$.H$_2$O (8.1 mg, 10 μmol) and 2,6-dichlorobenzoic acid (57.3 mg, 0.30 mmol) in CH$_3$CN (7 ml) was added H$_2$O$_2$ (30 μl of a 50% aq. solution, 0.53 mmol) at room temperature and the resulting mixture was stirred for 20 min. Subsequently, 1-octyne (1.10 g, 10 mmol) was added together with CH$_3$CN (3 ml). H$_2$O$_2$ (3.80 ml of a 50% aq. solution, 67 mmol) was then added at room temperature using a syringe pump (0.14 ml/hr). A second amount of [Mn$_2$O$_3$(Me$_3$-TACN)$_2$] (PF$_6$)$_2$.H$_2$O (8.1 mg, 10 μmol) was added to the reaction mixture 17.5 hours after the addition of hydrogen peroxide had commenced. When the addition of hydrogen peroxide was completed, the mixture was stirred for an additional hour. Water (10 ml) and diethyl ether (10 ml) were added and the pH of the aqueous layer was set to pH >10 by adding some 4 M NaOH (aq.). The organic layer was separated and the aqueous layer was washed with diethyl ether (3×15 ml). The pH of the aqueous layer was subsequently set to pH <1.5 with some 10% HCl (aq.) and was extracted with diethyl ether (5×10 ml). The combined extracts were washed with brine (15 ml) and subsequently dried over anhydrous Na$_2$SO$_4$. The solvents were evaporated in vacuo yielding 0.238 g of a solid with a purity of circa 86% (determined by $^1$H NMR). Heptanoic acid was thus obtained in about 16% yield. $^1$H NMR (400 MHz, acetone-d6): δ 0.90-0.97 (m, 3H), 1.34-1.38 (m, 6H), 1.58-1.65 (m, 2H), 2.29-2.33 (m, 2H). N.B. NMR showed other compounds as well, including 2,6-dichlorobenzoic acid.

Experiment 6

Phenylacetylene→Benzoic Acid

To a mixture of [Mn$_2$O$_3$(Me$_3$-TACN)$_2$] (PF$_6$)$_2$.H$_2$O (8.1 mg, 10 μmol) and 2,6-dichlorobenzoic acid (57.3 mg, 0.30 mmol) in CH$_3$CN (7 ml) was added H$_2$O$_2$ (30 μl of a 50% aq. solution, 0.53 mmol) at room temperature and the resulting mixture was stirred for 20 min. Subsequently, phenylacetylene (1.02 g, 10 mmol) was added together with CH$_3$CN (3 ml). H$_2$O$_2$ (3.80 ml of a 50% aq. solution, 67 mmol) was then added at room temperature using a syringe pump (0.14 ml/hr). A second amount of [Mn$_2$O$_3$(Me$_3$-TACN)$_2$] (PF$_6$)$_2$.H$_2$O (8.1 mg, 10 μmol) was added to the reaction mixture 17.5 hours after the addition of hydrogen peroxide had commenced. Upon addition of this second batch of catalyst: a lot of catalase activity (hydrogen peroxide decomposition) and heat formation, which resulted in a loss of the reaction volume by about 50%. When the addition of hydrogen peroxide was completed, the mixture was stirred for an additional hour. Water (10 ml) and diethyl ether (10 ml) were added and the pH of the aqueous layer was set to pH >10 by adding some 4 M NaOH (aq.). The organic layer was separated and the aqueous layer was washed with diethyl ether (3×15 ml). The pH of the aqueous layer was subsequently set to pH <1.5 with some 10% HCl (aq.) and was extracted with diethyl ether (5×10 ml). The combined extracts were washed with brine (15 ml) and subsequently dried over anhydrous Na$_2$SO$_4$. The solvents were evaporated in vacuo yielding 0.333 g of a solid with a purity of circa 54% (determined by $^1$H NMR). Benzoic acid was thus obtained in about 15% yield. $^1$H NMR (400 MHz, acetone-d6): δ 7.53-7.57 (m, 2H), 7.65-7.69 (m, 1H), 8.08-8.10 (m, 2H). N.B. NMR showed other compounds as well, including 2,6-dichlorobenzoic acid.

Experiment 7

1-methyl-1-cyclohexene→6-oxoheptanoic acid

To a mixture of [Mn$_2$O$_3$(tmtacn)$_2$] (PF$_6$)$_2$.H$_2$O (8.1 mg, 10 μmol) and 2,6-dichlorobenzoic acid (57.3 mg, 0.30 mmol) in CH$_3$CN (7 ml) was added H$_2$O$_2$ (30 μl of a 50% aq. solution, 0.53 mmol) at room temperature and the resulting mixture was stirred for 20 min. Subsequently 1-methyl-1-cyclohexene (962 mg, 10 mmol) was added together with CH$_3$CN (3 ml). H$_2$O$_2$ (3.22 ml of a 50% aq. solution, 56.8 mmol) was then added at room temperature using a syringe pump (0.14 ml/hr). A second amount of $[Mn_2O_3(tmtacn)_2]$ $(PF_6)_2.H_2O$ (8.1 mg, 10 µmol) was added to the reaction mixture 6.5 hours after the addition of hydrogen peroxide had commenced and a third amount of $[Mn_2O_3(tmtacn)_2]$ $(PF_6)_2.H_2O$ (8.1 mg, 10 µmol) was added to the reaction mixture 18 hours after the addition of hydrogen peroxide had commenced. When the addition of hydrogen peroxide was completed, the mixture was stirred for an additional hour. Water (10 ml) and diethyl ether (10 ml) were added to the combined filtrates, followed by solid sodium bisulfite (ca. 1 gram) to remove excess $H_2O_2$ (removal was confirmed by commercially available peroxide test strips). The pH of the aqueous layer was set to pH >10 by adding some solid NaOH. The organic layer was separated and the aqueous layer was washed with diethyl ether (3×15 ml). The pH of the aqueous layer was subsequently set to pH <1.5 with some 35% HCl (aq.) and was extracted with diethyl ether (5×10 ml). The combined extracts were washed with brine (15 ml) and subsequently dried over anhydrous $Na_2SO_4$. The solvents were evaporated in vacuo yielding 146 mg of a solid with a purity of circa 14% (determined by $^1H$ NMR). 6-Oxoheptanoic acid was thus obtained in about 1.4% yield. $^1H$ NMR (400 MHz, acetone-d6): δ 1.55-159 (m, 4H), 2.08 (s, 3H), 2.27-2.31 (m, 2H), 2.46-2.49 (m, 2H). Purity was confirmed with GC (FID detector). GC-MS (EI) showed the presence of 6-oxoheptanoic acid as well: m/z 144.1 [M+], 126.0, 111.0, 98.0, 84.0, 73.0, 58.0, 43.0.
N.B. NMR showed other compounds as well, including 2,6-dichlorobenzoic acid.

Experiment 8

Cyclooctene→Suberic Acid

To a mixture of $[Mn_2O_3(Me_3\text{-TACN})_4]$ $(PF_6)_2.H_2O$ (8.1 mg, 10 µmol, 0.1 mol %) and 2,6-dichlorobenzoic acid (57.3 mg, 0.30 mmol, 3.0 mol %) in $CH_3CN$ (7 ml) was added $H_2O_2$ (30 µl of a 50% aq. solution, 0.53 mmol) at room temperature and the resulting mixture was stirred for 20 min. Subsequently cyclooctene (1.16 g, 10 mmol) was added together with $CH_3CN$ (2 ml) and water (1 ml). $H_2O_2$ (2.83 ml of a 50% aq. solution, 50 mmol, 5.0 equiv.) was then added at room temperature using a syringe pump (0.07 ml/h). New batches of $[Mn_2O_3(Me_3\text{-TACN})_2]$ $(PF_6)_2.H_2O$ (8.1 mg, 10 µmol, 0.1 mol % per batch) were added to the reaction mixture 17, 25 and 40.5 hours after the addition of $H_2O_2$ had commenced. When the addition of $H_2O_2$ was completed, the mixture was stirred for additional 1 hour. Water (10 ml) and $Et_2O$ (10 ml) were added and the pH of the aqueous layer was set to pH >9 by adding some saturated $NaHCO_3$ (aq.). The organic layer was separated and the aqueous layer was washed with $Et_2O$ (3×15 ml). The pH of the aqueous layer was subsequently set to pH <2 with some 10% HCl (aq.) and was extracted with $Et_2O$ (3×20 ml). The combined organic extracts were dried over anhydrous $Na_2SO_4$. The solvents were removed in vacuo yielding 868 mg of a solid with a purity of circa 95% (determined by $^1H$ NMR), 47% yield of suberic acid. $^1H$ NMR (400 MHz, acetone-d6) δ 1.34-1.39 (m, 4H), 1.56-1.63 (m, 4H), 2.28 (t, J=7.4, 4H). N.B. NMR showed other compounds as well, including 2,6-dichlorobenzoic acid.

Experiment 9

Cyclohexene→Adipic Acid

To a mixture of $[Mn_2O_3(Me_3\text{-TACN})_2]$ $(PF_6)_2.H_2O$ (16.2 mg, 20 µmol, 0.2 mol %) and 2,6-dichlorobenzoic acid (57.3 mg, 0.30 mmol, 3.0 mol %) in $CH_3CN$ (7 ml) was added $H_2O_2$ (30 µl of a 50% aq. solution, 0.53 mmol) at room temperature and the resulting mixture was stirred for 20 min. Subsequently cyclohexene (0.805 g, 9.70 mmol) was added together with $CH_3CN$ (2 ml) and water (1 ml). $H_2O_2$ (5.67 ml of a 50% aq. solution, 100 mmol, 10.0 equiv.) was then added at 60° C. using a syringe pump (0.7 ml/h). New batches of $[Mn_2O_3(Me_3\text{-TACN})_2]$ $(PF_6)_2.H_2O$ (16.2 mg, 20 µmol, 0.2 mol % per batch) were added to the reaction mixture 1.5, 3.5, 5 and 7 hours after the addition of $H_2O_2$ had commenced. When the addition of $H_2O_2$ was completed, the mixture was stirred for additional 15 hours. Water (10 ml) and $Et_2O$ (10 ml) were added and the pH of the aqueous layer was set to pH >9 by adding some saturated $NaHCO_3$ (aq.). The organic layer was separated and the aqueous layer was washed with $Et_2O$ (3×15 ml). The pH of the aqueous layer was subsequently set to pH <2 with some 10% HCl (aq.) and was extracted with $Et_2O$ (3×20 ml). The combined organic extracts were dried over anhydrous $Na_2SO_4$. The solvents were removed in vacuo yielding 473 mg of a solid with a purity of circa 56% (determined by $^1H$ NMR), 18% yield of adipic acid. N.B. NMR showed other compounds as well, including 2,6-dichlorobenzoic acid.

Experiment 10

Cyclooctene→Suberic Acid

To a mixture of $[Mn_2O_3(Me_3\text{-TACN})_2]$ $(PF_6)_2.H_2O$ (16.2 mg, 20 µmol, 0.2 mol %) and 2,6-dichlorobenzoic acid (57.3 mg, 0.30 mmol, 3.0 mol %) in 2-butanone (7 ml) was added $H_2O_2$ (30 µl of a 50% aq. solution, 0.53 mmol) at room temperature and the resulting mixture was stirred for 20 min. Subsequently cyclooctene (1.149 g, 9.90 mmol) was added together with 2-butanone (2 ml) and water (1 ml). $H_2O_2$ (5.67 ml of a 50% aq. solution, 100 mmol, 10.0 equiv.) was then added at 40° C. using a syringe pump (0.7 ml/h). New batches of $[Mn_2O_3(Me_3\text{-TACN})_2]$ $(PF_6)_2.H_2O$ (16.2 mg, 20 µmol, 0.2 mol % per batch) were added to the reaction mixture 1.5, 3, 4.5, 6 and 7.5 hours after the addition of $H_2O_2$ had commenced. When the addition of $H_2O_2$ was completed, the mixture was stirred for additional 15 hours. Water (10 ml) and $Et_2O$ (10 ml) were added and the pH of the aqueous layer was set to pH >9 by adding some saturated $NaHCO_3$ (aq.). The organic layer was separated and the aqueous layer was washed with $Et_2O$ (3×15 ml). The pH of the aqueous layer was subsequently set to pH <2 with some 10% HCl (aq.) and was extracted with $Et_2O$ (3×20 ml). The combined organic extracts were dried over anhydrous $Na_2SO_4$. The solvents were removed in vacuo yielding 926 mg of a solid with a purity of circa 74% (determined by $^1H$ NMR), 40% yield of suberic acid. N.B. NMR showed other compounds as well, including 2,6-dichlorobenzoic acid.

Experiment 11

Cyclooctene→Suberic Acid

To a mixture of $[Mn_2O_3(Me_3\text{-TACN})_2]$ $(PF_6)_2.H_2O$ (16.2 mg, 20 µmol) and trichloroacetic acid (32.7 mg, 0.20 mmol) in $CH_3CN$ (14 ml) was added $H_2O_2$ (60 µl of a 50% aq. solution, 1.06 mmol) at room temperature and the resulting mixture was stirred for 20 min. Subsequently cyclooctene (20 mmol) was added together with $CH_3CN$ (4 ml) and water (2 ml). $H_2O_2$ (4.53 ml of a 50% aq. solution, 80 mmol) was then added at room temperature using a syringe pump (0.14 ml/hr). A second amount of $[Mn_2O_3(Me_3\text{-TACN})_2]$ $(PF_6)_2.H_2O$ (16.2 mg, 20 µmol) was added to the reaction mixture 17 hours after the addition of hydrogen peroxide had commenced and a third amount of [Mn$_2$O$_3$(Me$_3$-TACN)$_2$] (PF$_6$)$_2$.H$_2$O (16.2 mg, 20 μmol) was added to the reaction mixture 24 hours after the addition of hydrogen peroxide had commenced. When the addition of hydrogen peroxide was completed, the mixture was stirred for an additional 6 hours. Water (10 ml) and diethyl ether (10 ml) were added and the pH of the aqueous layer was set to pH >10 by adding some 4 M NaOH (aq.). The organic layer was separated and the aqueous layer was washed with diethyl ether (3×15 ml). The pH of the aqueous layer was subsequently set to pH <1.5 with some 10% HCl (aq.) and was extracted with diethyl ether (5×10 ml). The combined extracts were washed with brine (15 ml) and subsequently dried over anhydrous Na$_2$SO$_4$. The solvents were evaporated in vacuo yielding 0.279 g of a solid with a purity of circa 58% (determined by $^1$H NMR). Suberic acid was thus obtained in about 4.6% yield. $^1$H NMR (400 MHz, acetone-d6): δ 1.39-1.45 (m, 4H), 1.63-1.66 (m, 4H), 2.33 (t, J=7.3 Hz, 4H), 10.5 (br s, 2H). N.B. NMR showed other compounds as well.

Comparative Experiment

Cyclooctene→Suberic Acid

To a solution of [Mn$_2$O$_3$(Me$_3$-TACN)$_2$] (PF$_6$)$_2$.H$_2$O (16.2 mg, 20 μmol) in CH$_3$CN (14 ml) was added H$_2$O$_2$ (60 μl of a 50% aq. solution, 1.06 mmol) at room temperature and the resulting mixture was stirred for 20 min. Subsequently cyclooctene (20 mmol) was added together with CH$_3$CN (4 ml) and water (2 ml). H$_2$O$_2$ (4.53 ml of a 50% aq. solution, 80 mmol) was then added at room temperature using a syringe pump (0.14 ml/hr). A second amount of [Mn$_2$O$_3$(Me$_3$-TACN)$_2$] (PF$_6$)$_2$.H$_2$O (16.2 mg, 20 μmol) was added to the reaction mixture 17 hours after the addition of hydrogen peroxide had commenced and a third amount of [Mn$_2$O$_3$(Me$_3$-TACN)$_2$] (PF$_6$)$_2$.H$_2$O (16.2 mg, 20 μmol) was added to the reaction mixture 24 hours after the addition of hydrogen peroxide had commenced. When the addition of hydrogen peroxide was completed, the mixture was stirred for an additional 6 hours. Water (10 ml) and diethyl ether (10 ml) were added and the pH of the aqueous layer was set to pH >10 by adding some 4 M NaOH (aq.). The organic layer was separated and the aqueous layer was washed with diethyl ether (3×15 ml). The pH of the aqueous layer was subsequently set to pH <1.5 with some 10% HCl (aq.) and was extracted with diethyl ether (5×10 ml). The combined extracts were washed with brine (15 ml) and subsequently dried over anhydrous Na$_2$SO$_4$. The solvents were evaporated in vacuo yielding 41 mg of a solid with a purity of circa 43% (determined by $^1$H NMR). Suberic acid was thus obtained in about 0.5% yield (average of two runs). $^1$H NMR (400 MHz, acetone-d6): δ 1.39-1.43 (m, 4H), 1.61-1.68 (m, 4H), 2.33 (t, J=7.5 Hz, 4H), 10.5 (br s, 2H). N.B. NMR showed other compounds as well.

We claim:

1. A one-pot method for providing a carboxylic acid or a ketone-containing compound, the method comprising:
   contacting an alkene or an alkyne with a catalytic oxidation system to form a reaction mixture, wherein the catalytic oxidation system comprises:
   (i) hydrogen peroxide,
   (ii) a manganese transition metal catalyst having a ligand of formula (I):

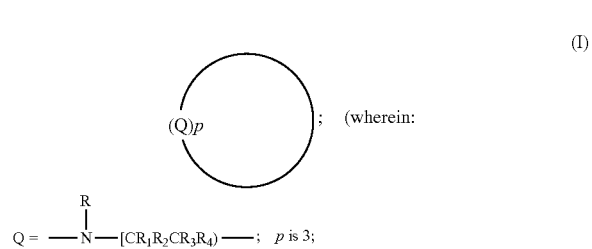

(wherein:
   R is independently selected from the group consisting of: hydrogen, C$_1$-C$_6$-alkyl, CH$_3$CH$_2$OH, CH$_3$COOH, and pyridin-2-ylmethyl, and optionally one of R is linked to the N of another Q from another ring via an ethylene or propylene bridge; R$_1$, R$_2$, R$_3$, and R$_4$ are independently selected from the group consisting of: H, C$_1$-C$_4$-alkyl, and C$_1$-C$_4$-alkylhydroxy;
   (iii) a carboxylic acid, carboxylate salt or mixture thereof; or ascorbic acid, or a salt or ester thereof, or mixture thereof; and
   wherein the molar ratio of hydrogen peroxide to the alkene or the alkyne is from 20:1 to 1:1, and the manganese transition metal catalyst is present in a range from 0.0001 to 5 mol % with respect to the alkene or the alkyne; and
   forming a second carboxylic acid or a ketone-containing compound.

2. The method of claim 1 wherein, one of R is linked to the N of another Q from another ring via an ethylene bridge.

3. The method of claim 1, wherein the molar ratio of hydrogen peroxide to the alkene or the alkyne is from 20:1 to 4:1.

4. The method of claim 1, wherein the molar ratio of hydrogen peroxide to the alkene or the alkyne is from 10:1 to 2:1.

5. The method of claim 4, wherein the molar ratio of hydrogen peroxide to the alkene or the alkyne is from 6:1 to 3:1.

6. The method of claim 1, wherein the manganese transition metal catalyst is present in a range from 0.001 and 1 mol % with respect to the alkene or the alkyne.

7. The method of claim 1, wherein the ligand is 1,4,7-trimethyl-1,4,7-triazacyclononane (Me$_3$-TACN) or 1,2-bis-(4,7-dimethyl-1,4,7-triazacyclonon-1-yl)-ethane (Me$_4$-DTNE).

8. The method of claim 1, wherein the manganese transition metal catalyst is a dinuclear complex having two manganese ions of the oxidation state selected from II-II, II-III, III-III, III-IV, and IV-IV, and one or more oxygen or carboxylate bridges between the two manganese ions.

9. The method of claim 1, wherein the manganese transition metal catalyst is a salt of [(Mn$^{IV}$)$_2$(μ-O)$_3$(Me$_3$-TACN)$_2$]$^{2+}$, a salt of [(Mn$^{III}$)$_2$(μ-O)(μ-CH$_3$COO)$_2$(Me$_3$-TACN)$_2$)]$^{2+}$ or a salt of [Mn$^{III}$Mn$^{IV}$(μ-O)$_2$(μ-CH$_3$COO)(Me$_4$-DTNE)]$^{2+}$.

10. The method of claim 1, wherein the component (iii) of the catalytic oxidation system comprises the carboxylic acid, the carboxylate salt, or the mixture of a carboxylic acid and carboxylate salt.

11. The method of claim 1, wherein component (iii) of the catalytic oxidation system comprises ascorbic acid, or a salt or ester thereof, or mixture thereof.

12. The method of claim 11, wherein component (iii) of the catalytic oxidation system further comprises a carboxylic acid, a carboxylate salt, or a mixture thereof.

13. The method of claim 1, wherein the carboxylic acid or carboxylate salt is selected from the group consisting of: oxalic acid, benzoic acid, 2,6-dichlorobenzoic acid and trichloroacetic acid.

14. The method of claim 1, wherein the carboxylic acid in component (iii) is the same as the second carboxylic acid.

15. The method of claim 1, wherein the contacting is carried out in the presence of solvent selected from the group consisting of: acetonitrile, methanol, ethanol, t-butanol, methylethylketone, and water.

16. The method of claim 1, further comprising working up the reaction mixture with or without purification.

17. The method of claim 1, wherein the second carboxylic acid is a dicarboxylic acid.

18. The method of claim 1, wherein the alkene or the alkyne is subjected to oxidative cleavage in the reaction mixture.

19. The method of claim 18, wherein the alkene has at least one vinylic hydrogen.

20. The method of claim 19, wherein the alkene has at least two vinylic hydrogens.

21. The method of claim 20, wherein the alkene further has only one carbon-carbon double bond.

22. The method of claim 21, wherein the alkene is monocyclic.

23. The method of claim 22, wherein the alkene is cyclooctene or cyclohexene.

24. The method of claim 23, wherein the alkene is cyclohexene and the second carboxylic acid is adipic acid.

25. The method of claim 16, further comprising contacting the reaction mixture with the catalytic oxidation system after working up the reaction mixture.

* * * * *